United States Patent
Lenox et al.

[11] Patent Number: 5,865,731
[45] Date of Patent: Feb. 2, 1999

[54] SURGICAL RETRACTOR HAVING VARIABLE POSITION RETRACTOR BLADES

[75] Inventors: Linda Kathleen Lenox, Boulder; Carl A. Schmidt, Denver, both of Colo.

[73] Assignee: Lenox-MacLaren, Boulder, Colo.

[21] Appl. No.: 787,343

[22] Filed: Jan. 25, 1997

[51] Int. Cl.⁶ .................................................. A61B 17/00
[52] U.S. Cl. .......................................................... 600/232
[58] Field of Search .................................. 600/201, 227, 600/231, 232, 234

[56] References Cited

U.S. PATENT DOCUMENTS

| | | |
|---|---|---|
| 3,710,783 | 1/1973 | Jascalevich . |
| 3,747,592 | 7/1973 | Santos . |
| 3,810,462 | 5/1974 | Szpur . |
| 4,627,421 | 12/1986 | Symbas et al. . |
| 4,726,356 | 2/1988 | Santilli et al. . |
| 4,798,195 | 1/1989 | Seare, Jr. . |
| 4,829,985 | 5/1989 | Couetil ................................... 600/232 |
| 4,852,552 | 8/1989 | Chaux ................................. 600/234 X |
| 4,865,019 | 9/1989 | Phillips ................................... 600/232 |
| 4,989,587 | 2/1991 | Farley . |
| 5,025,779 | 6/1991 | Bugge ................................. 600/232 X |
| 5,088,472 | 2/1992 | Fakhrai . |
| 5,167,223 | 12/1992 | Koros et al. . |
| 5,280,782 | 1/1994 | Wilk . |
| 5,295,994 | 3/1994 | Bonutti ................................... 606/192 |
| 5,297,538 | 3/1994 | Daniel . |
| 5,363,841 | 11/1994 | Coker . |
| 5,365,921 | 11/1994 | Bookwalter et al. . |
| 5,503,617 | 4/1996 | Jako ......................................... 600/201 |
| 5,512,038 | 4/1996 | O'Neal et al. ........................... 600/210 |
| 5,514,076 | 5/1996 | Ley ......................................... 600/206 |
| 5,514,153 | 5/1996 | Bonutti ................................... 606/190 |
| 5,520,608 | 5/1996 | Cabrera et al. ........................ 600/201 |
| 5,522,790 | 6/1996 | Moll et al. .............................. 600/204 |
| 5,529,571 | 6/1996 | Daniel .................................... 600/219 |
| 5,558,621 | 9/1996 | Heil ........................................ 600/226 |

FOREIGN PATENT DOCUMENTS

| | | | |
|---|---|---|---|
| 3834358 | 4/1990 | Germany ................................ 600/232 |

OTHER PUBLICATIONS

"The USSC Mini–CABG Access Set", USSC Publication, vol. 1, No. 1, Nov., 1996.
"Beating Heart Bypass", CTS Mid–Cab System Brochure, Copyright 1996.

*Primary Examiner*—Jeffrey A. Smith
*Attorney, Agent, or Firm*—Sheridan Ross P.C.

[57] ABSTRACT

A surgical retractor is disclosed that is able to form an oblique tunnel-like opening at an incision site wherein, in addition to spreading the sides of the site incision substantially parallel to the contour of the patient's body, the present surgical retractor additionally spreads the incision sides so that one side is depressed toward the patient and the other is directed outwardly from the patient. Accordingly, the present retractor is useful for forming a tunnel-like opening to, for example, the heart by obliquely spreading the patient's ribs. Further, the present retractor is particularly useful in keyhole or mini-surgery wherein the initial incision site is not immediately adjacent to the target surgery site.

26 Claims, 6 Drawing Sheets

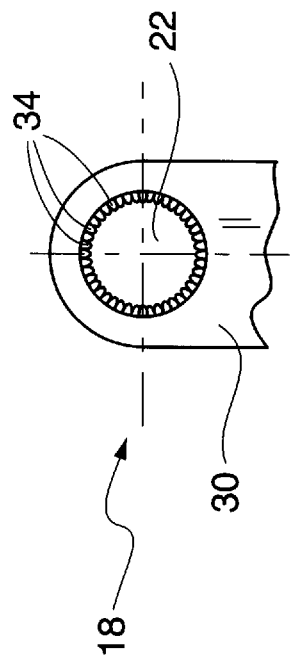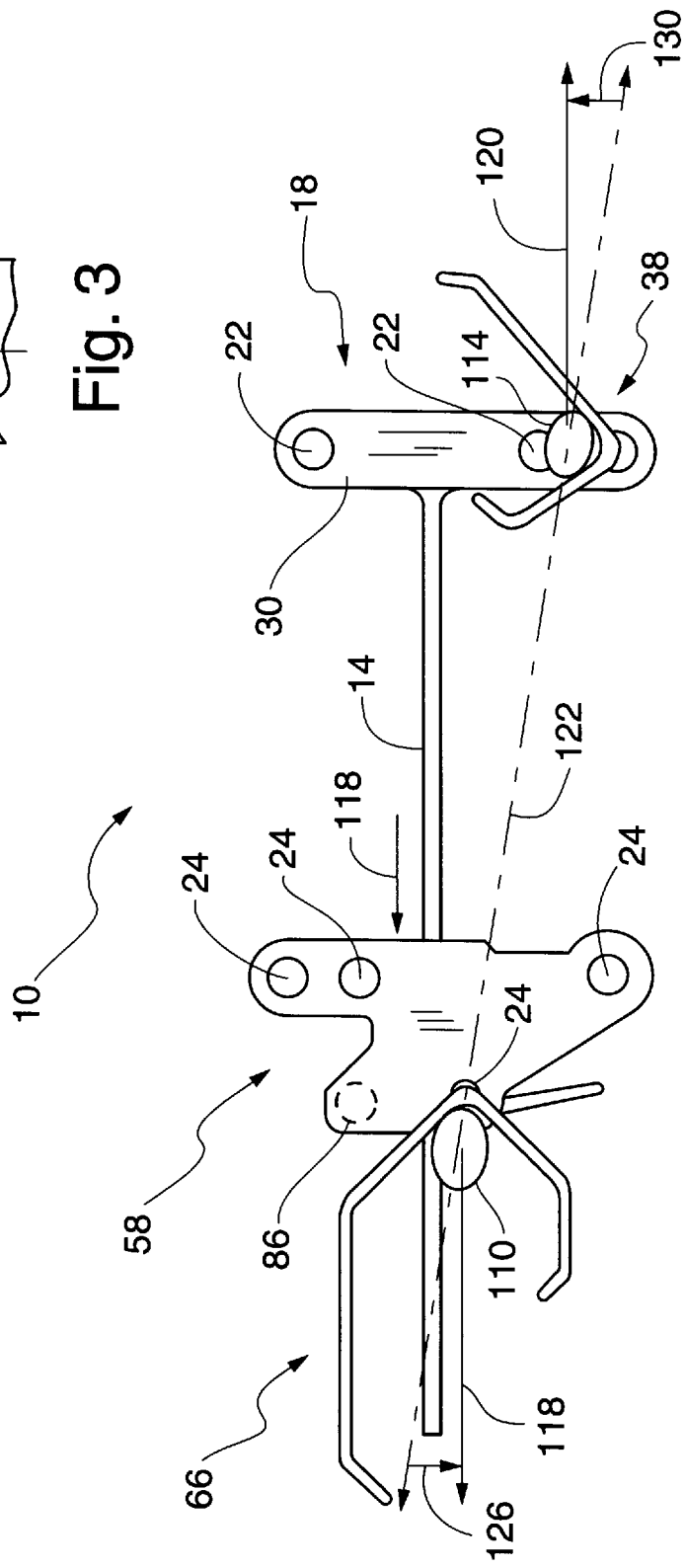

SURGICAL RETRACTOR HAVING VARIABLE POSITION RETRACTOR BLADES

FIELD OF THE INVENTION

The present invention relates to a signal retractor, and in particular, a surgical retractor capable of forming an oblique tunnel-like opening at an incision site so that one side of the site is depressed and another side is raised.

BACKGROUND OF THE INVENTION

During a surgical procedure, it is usually mandatory to maintain the sides of an incision apart from one another so that interior organs are maintained accessible during a surgery by providing retractor grips for gripping and spreading the sides of a surgical incision. Accordingly, various surgical retractors have been utilized to maintain a surgical incision opening. However, heretofore, no such retractor has provided the ability to easily create and maintain an oblique surgical incision opening wherein the sides of the incision are not only separated substantially along contour of the patient's body, but also in two opposite directions, these two directions being substantially normal to the contour of the patient's body. For example, it is not uncommon for the grips of a retractor to have a single fixed orientation and a single lateral degree of movement for moving the sides of an incision apart generally in directions following the contour of the patient's body surrounding the incision. Such retractors become especially troublesome in recently developed surgical techniques wherein the surgical incision is relatively small and may be somewhat displaced from the most direct access to a desired surgical site. In such surgical techniques (sometimes known as "keyhole surgery" or "mini-surgery"), the most desirable configuration for the surgical opening may not be simply a lateral spacing apart of the sides of the surgical incision. Instead, an oblique opening may be desired, wherein one side of the surgical incision is raised above the other so that, for example, a short tunnel or cavity may be created to the internal area of the patient to which the surgery is directed. Accordingly, it would be advantageous to have a surgical retractor that alleviates the above-identified difficulties of prior surgical retractors.

SUMMARY OF THE INVENTION

The present invention is a surgical retractor that is adjustable so that the surgical incision grips can grip the sides of a surgical incision at any one of a plurality of orientations and that the grips can be caused to move obliquely relative to the contour of a patient's body. That is, during the process of opening a surgical incision with the retractor of the present invention, the retraction process also causes one of the grips to direct the incision site it is gripping to a position somewhat inwardly toward the patient's body, and the other grip is directed somewhat outwardly from the patient's body. Thus, an oblique surgical incision opening may be maintained by the retractor of the present invention.

It is an additional aspect of the present invention that the present surgical retractor have detachable and replaceable members that allow the retractor to more effectively fit the patient's contour, body type, body size and the surgical procedure being performed. That is, the surgical retractor of the present invention includes replaceable, differently configured retractor levers. For example, although each such lever has a corresponding arm and a tissue grip attached to one end of the arm, the length of the arm and the size and shape of the tissue grip may vary between retractor levers. Furthermore, the retractor levers can be rotatably positioned in the retractor in use wherein each such retractor lever can, when in use, have its tissue gripper set at a rotational orientation relative to a longitudinal axis of its arm independently of any other retractor lever also being used. Thus, the retractor levers may be configured to accommodate the patient's body and the incision for retraction. Further, the retractor of the present invention can be adjusted so that the tissue grips of its retractor levers may be positioned for gripping portions of the sides of the incision that are directly adjacent to one another, or the tissue grips may be positioned for gripping portions of the sides of the incision that are offset from one another along the length of the incision.

Other features and advantages to the present invention will become evident from the detailed description and the drawings included herein.

BRIEF DESCRIPTION OF THE DRAWINGS

FIG. 2 is an exemplary view of a bore 22 as viewed face-on from the surface 30 where the retractor lever 38 is inserted;

FIG. 3 illustrates the use of the present invention in spreading two adjacent ribs of a patient apart, wherein this figure illustrates the forces induced on the ribs by the surgical retractor of the present invention;

DETAILED DESCRIPTION OF A PREFERRED EMBODIMENT OF THE INVENTION

Figure 1:
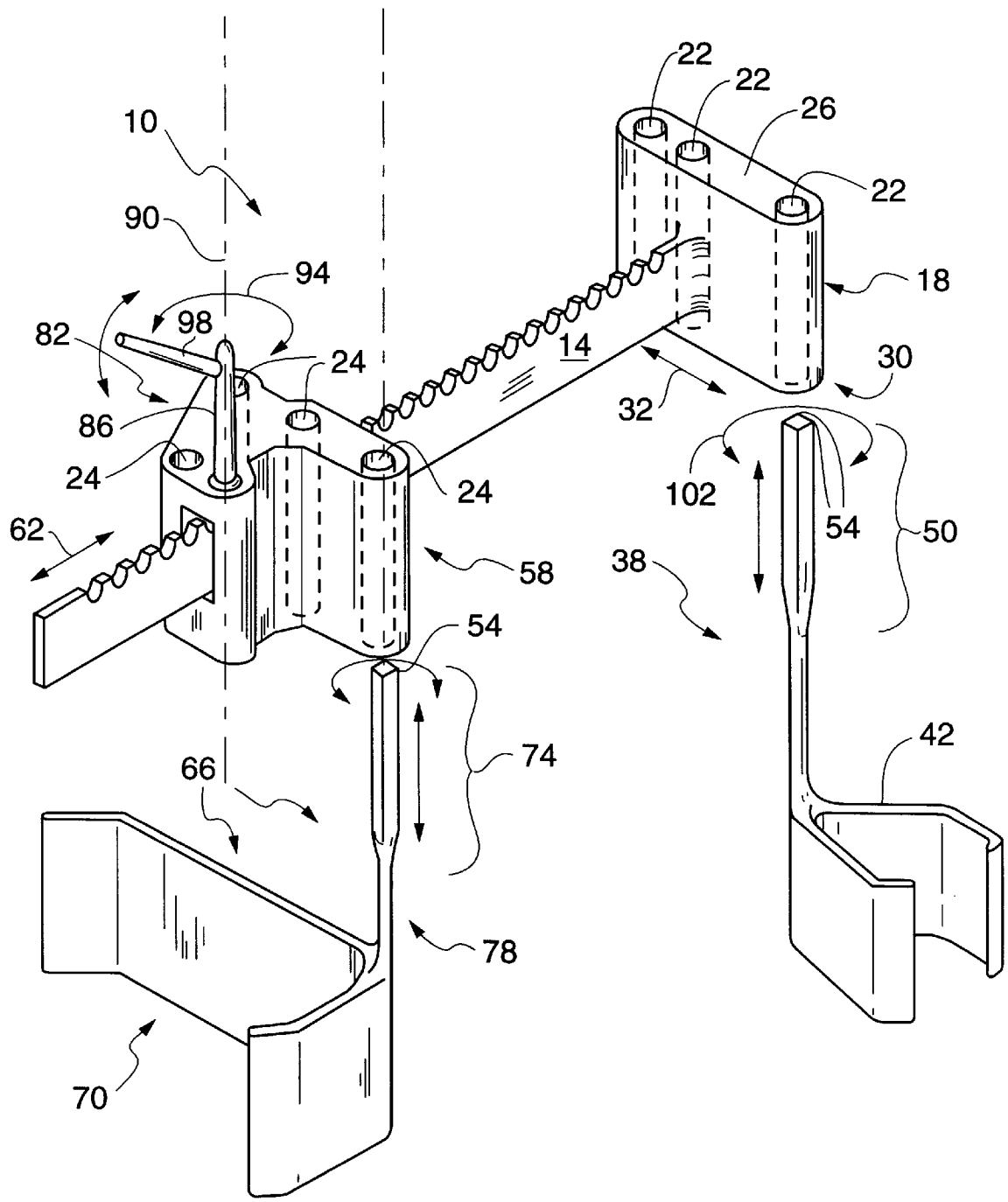
FIG. 1 is a perspective view of the surgical retractor 10 of the present invention illustrating how the retractor levers 38 and 66 may be attached to the main body of the surgical retractor 10 prior to use.

In FIG. 1, an embodiment of the surgical retractor 10 of the present invention is illustrated. The retractor 10 includes a toothed crossbar 14 fixedly attached to a stationary head 18 at one end of the crossbar 14. The stationary head 18 is preferably attached to the crossbar in an offset manner as is best shown in FIG. 3, wherein a length of the stationary head 18 on one side of crossbar 14 is longer than the length of the other side of the crossbar. Provided in the stationary head 18 are a plurality of bores 22, preferably at least three, that penetrate the thickness of the stationary head 18 and accordingly have corresponding openings on the upper head surface 26 and the lower head surface 30. Note that the bores 22 are positioned at different vector offsets from the crossbar 14 along a length of the stationary head 18 in the directions of the double headed arrow 32. Further note the length of stationary head 18 is oriented substantially transversely to the length of crossbar 14 (e.g., in the direction of arrow 62). However, in an alternative embodiment the stationary head 18 is adjustable with respect to the crossbar 14; for example, the head 18 can be fixedly positioned at various angles with respect to the crossbar 14. Using appropriate pivoting mounting means, the head 18 can be adjusted so that it is fixed in a desired three-dimensional orientation, thus permitting a surgeon to create a desired surgical opening without being constrained to movement within fixed planes.

As shown in FIG. 2, each of the bores 22 has an interior surface with a plurality of notches 34 surrounding the interior of each bore 22 and extending at least partially through the bore. The notches 34 can be numerous in number to facilitate various angular orientations of the grips 42 and 70 (see FIG. 2), but should number at least three.

A moveable retractor head 58 is operably connected to the crossbar 14 so that this head is moveable along the length of the crossbar (the movement as indicated by the double-headed arrow 62). The moveable retractor head 58 has at least one bore 24 that penetrates the moveable head 58. The bores 24 of the moveable retractor head 58 penetrate the moveable head in a similar manner to the bores 22 of the stationary head 18, and in one embodiment, bores 22 and 24 are substantially parallel. Additionally, the bores 24 also have notches 34 surrounding their interior surfaces and extending at least partially through the thickness of the moveable head. Moreover, the bores 24 are also offset at various vectors (i.e., distances and/or directions) from the crossbar 14 along the length of the moveable head (i.e., the length being, again, in the directions of arrow 32).

The present invention further includes retractor levers 38 and 66 for maintaining a surgical opening or incision by contacting the sides of the opening. The retractor lever 38 includes an arm 46 having, at one end, a mating portion 50 with a substantially uniform cross-section with at least one edge, and preferably a plurality of edges 54 for mating into the notches 34 of any one of the bores 22. Additionally, the retractor lever 38 includes a grip 42 for gripping, for example, a rib and adjacent tissue when the retractor 10 is utilized in, for example, surgery wherein adjacent ribs are spread apart, as one skilled in the art will understand. Thus, the retractor lever 38 may be fitted into a suitable one of the bores 22 in the stationary head 18 as is described hereinbelow. The retractor lever 66 is similar to lever 38. That is, retractor lever 66 has the same functional components as lever 38. That is, the retractor-lever 66 has an arm 68, a mating portion 74 and a grip 70. Thus, a rib and tissue adjacent an incision can be gripped by grip 70 when the mating portion 74 of the lever arm 78 is inserted into one of the bores 24 of the moveable head 58.

The moveable head 58 is adjustable along the toothed crossbar 14 by a crank assembly 82 (whose external features are shown in FIG. 1 and whose internal cranking mechanism is conventional). Note that the external portions of the crank 82 provide for rotation of the crank cylinder 86 about the axis 90 as illustrated by the double-headed arrow 94. However, to assure that a surgeon can effectively rotate the crank cylinder 86 wherein there may be physical obstructions near the crank cylinder 86, an adjustable crank handle 94 is provided which is pivotally attached to the crank cylinder 86 so that the handle can be moved both about the crank cylinder 86 according to double-headed arrow 94 and also through any plane that also includes axis 90. Thus, the crank handle 98 moves in three dimensions and can be used to adjust the position of the moveable head 58 even when there are nearby obstructions.

By placing the retractor levers 38 and 66 in a bore 22 and 24 respectively of the stationary head 18 and the moveable head 58, respectively, adjacent ribs and surrounding tissue captured within the grips 42 and 70, respectively, can be separated when the moveable head 58 travels along the toothed crossbar 14 away from the stationary head 18. Further, since the mating portions 50 and 74 can have their respective edges 54 mated with notches 34 in any one of a number of orientations of their respective bores, the retractor levers can be configured in any one of a number of rotational positions about an axis (running lengthwise between the mating portion end and the grip end) of their respective arms. That is, the retractor levers 34 and 66 can be rotationally positioned according to double-headed arrows 102 and 106, respectively, and then fitted into respective bores 22 and 24. Further, since the mating portions 50 and 74 slide within the bores 22 and 24, different lengths (e.g., at least about 1 inch, more preferably about 3 inches and most preferably at least about 5 inches) of these mating portions may be provided within (or through) their respective bores so that the grips 42 and 70 may be at different lengths from the toothed crossbar 14. Accordingly, the sides of a surgical incision gripped by the grips 42 and 70 need not be directly opposite one another.

Thus, the present invention allows the grips 42 and 70 to be independently oriented in three dimensions (i.e., rotated in two dimensions about their corresponding arms and slidably offset from the toothed crossbar 14 in the third dimension) for customizing the fitting of the retractor 10 to the contour of a surgical patient's body and the incisions made on the patient during surgery. A surgeon is able to create a desired retraction of a surgical opening between adjacent tissues and/or bones. Thus, by:

(a) determining a desired distance of each of the grips 42, 70 from the toothed crossbar 14;

(b) selecting a desired angle of the grips 42, 70 by appropriate rotational insertion of the mating portions 50, 74 into the respective toothed bores 22, 24; and (c) adjusting the distance between the stationary head 18 and the moveable retractor head 58, Accordingly, this facilitates access into relatively small openings by not only spreading apart surgical incision sides in one or two dimensions, as is possible with prior art, but also allows for a third dimensional adjustment. Thus, for example, a "tunnel-like" cavity can be created between a patient's ribs such that one rib is pushed down and another (e.g., adjacent) rib is raised up, while spreading the ribs apart laterally along a plane or contour of the patient's body.

Additionally, since the retractor levers 38 and 66 are removable, alternate retractor levers having different configurations of grips may also be used, thereby allowing the present invention to be tailored to both the body type and contours of a surgical patient and also to the type of surgical procedure being performed. In particular, substantially differently configured grips may be utilized depending upon patient's body contour, the amount of body fat on the patient, the size of the patient (e.g., adult versus child) and the surgical procedure being performed (e.g., cardiovascular versus thoracic).

FIG. 3 illustrates the present invention wherein two adjacent ribs 110 and 114 are being separated by the retractor 10 of the present invention due to the movement of the moveable head 58 in the direction 116. In particular, the present figure illustrates a particularly important aspect of the present invention in that by placing the retractor levers 38 and 66 into bores 22 and 24 at different distances from the toothed crossbar 14, the forces exerted upon the ribs 110 and 114 along the length of the toothed crossbar 14 (i.e., in the direction of arrow 62) may be substantially different. In particular, by decomposing the force vectors 118 and 120 exerted on the ribs by the retractor 10 (along the length of the crossbar 14) into force vectors relative to the axis 122 between the cross-sectional centers of the ribs, it can be seen that a component vector corresponding to the force vector 126 forces the rib 110 downward (i.e., toward the patient's body) while a force vector 130 applied to rib 114 forces this rib upward (i.e., away from the rest to the patient's body). Thus, assuming the axis 122 is substantially parallel to the contour of the rib cage between ribs 110 and 114, the configuration of the present invention in FIG. 3 not only separates the ribs along the axis 122 but also separates the ribs by lifting one and depressing the other. Thus, for example, by using the retractor 10 in cardiovascular surgery, a surgical opening exposing the patient's heart can be maintained, for performing effective cardiovascular surgery through a tunnel provided to the heart.

Note that various alternative embodiments to the description of the embodiment above are also within the scope of the present invention. For example, the stationary head 18 may be replaceable so that different configurations of bores 22 are made available. Similarly, alternative moveable heads 58 having different bore 24 configurations may be utilized. Note that, for example, by changing the heads 18 and/or 58, at least the head sizes may be made appropriate to the size of the patient (i.e, potentially small heads for a small patient). Additionally, in another embodiment, the notches 34 within one or both of the bores 22 and/or 24 may be rotatable to anyone of a plurality positions within the bore(s) such that the rotatable notches may be fixed in a desired orientation by, for example, a locking and unlocking lever (not shown). Thus, if during a surgical procedure, where the grips 42 and 70 are gripping the sides of an incision and it becomes desirable to rotate one or both of the grips, then the bore(s) may be unlocked, rotated and then relocked in a different position.

In another embodiment of the present invention, the crossbar 14 may be contoured along its length to conform to, for example, the contour(s) of a patient's body. Thus, the crossbar 14 may have an arcuate rather than a straight length.

In yet another embodiment, the stationary head 18 is rotatable at the attachment site with the crossbar 14 so that the bores can be rotated (about an axis, e.g., corresponding with the length of the crossbar 14) and locked to any one of a plurality of positions. For example, a separate crank (not shown) may be used for rotating the bores 22 while the retractor is in use, thereby providing a surgeon with the ability to adjust, e.g., the force vectors 126 and 130 without disengaging the retractor from the incision to make such adjustments.

Figure 4:
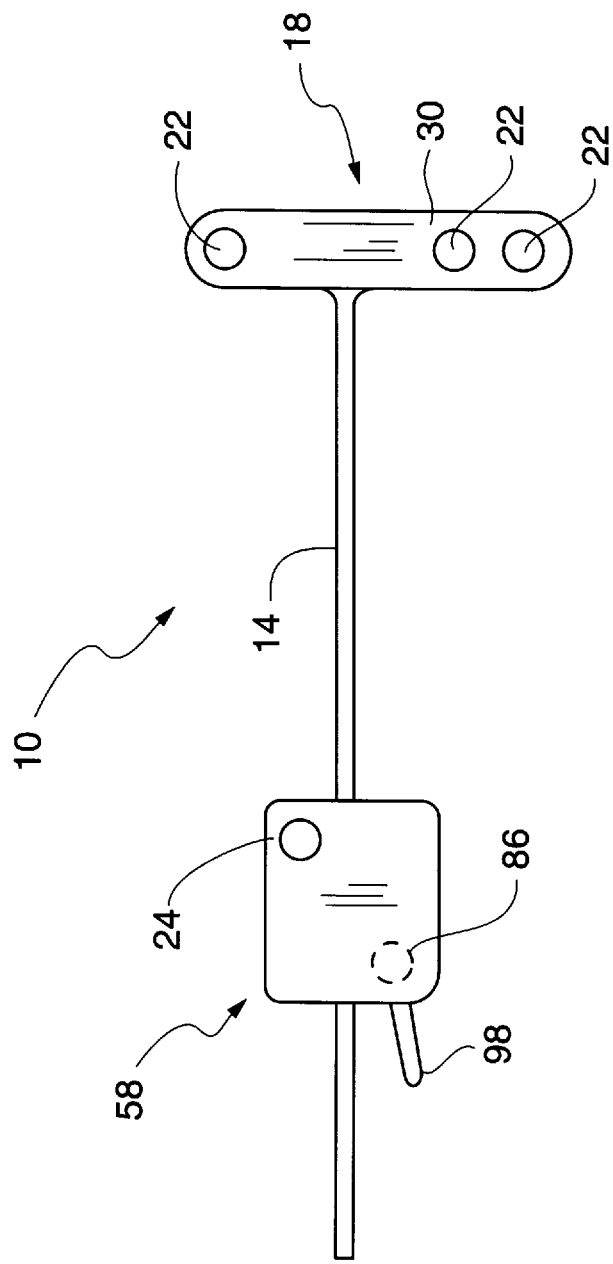
FIG. 4 illustrates an alternative embodiment of the present invention (without retractor levers being shown) wherein the moveable head 58 has only a single bore 24.
Figure 5:
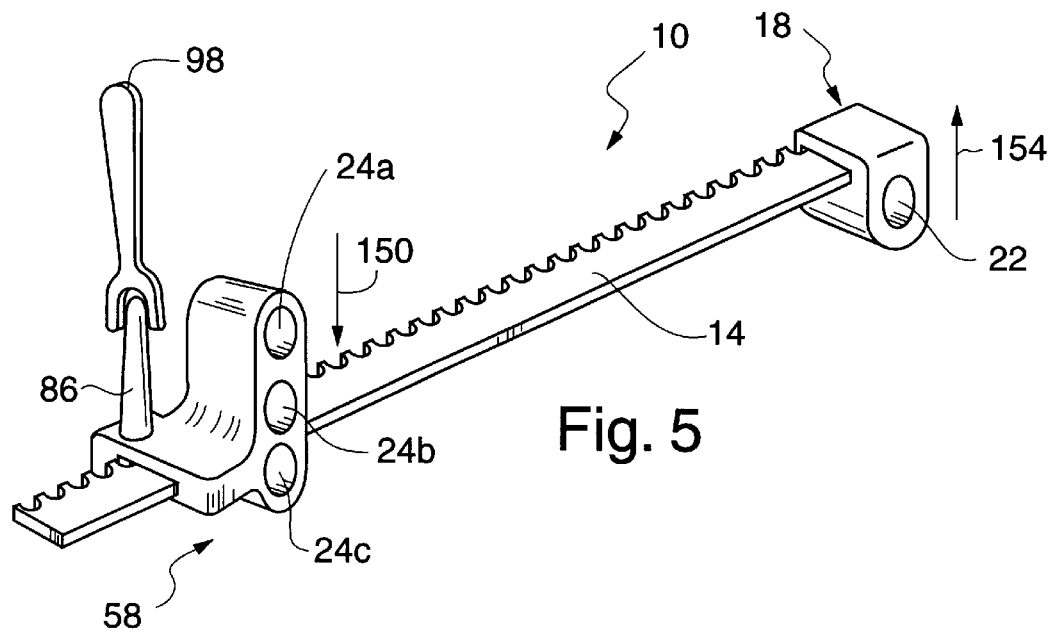
FIG. 5 is another alternative embodiment of the present invention (without the retractor levers being shown)

Alternative embodiments of the surgical retractor 10 are provided in FIGS. 4 and 5. In the embodiment of FIG. 4, there is a single bore 24 in the moveable head 58. In the embodiment of FIG. 5, there is a single bore 22 in the stationary head 18 and a plurality of bores 24 in the moveable head 58. Further, note that in this latter embodiment, the crank assembly 82 and the axis (of rotation) 90 are perpendicular the bores 22, 24 (instead of being parallel as in previous embodiments). Moreover, for one skilled in the art, various other embodiments will be apparent.

When using the present invention, a surgeon selects retractor levers appropriate to the patient and the surgical procedure, then the grips 42 and 70 of the selected retractor levers may be inserted into an incision so that each grip grasps an opposite side of the incision. Subsequently, after orienting the grips within the incision and adjusting the spacing between the stationary head 18 and the moveable head 58 (typically so that the heads are adjacent one another), the corresponding mating portions of the retractor levers are inserted into appropriate bores within the stationary head 18 and the moveable head 58 so that the desired orientation of the grips is maintained. Following this, the surgeon can commence retracting the sides of the incision by rotating the crank assembly 82 until the desired incision opening is obtained.

Figure 6:
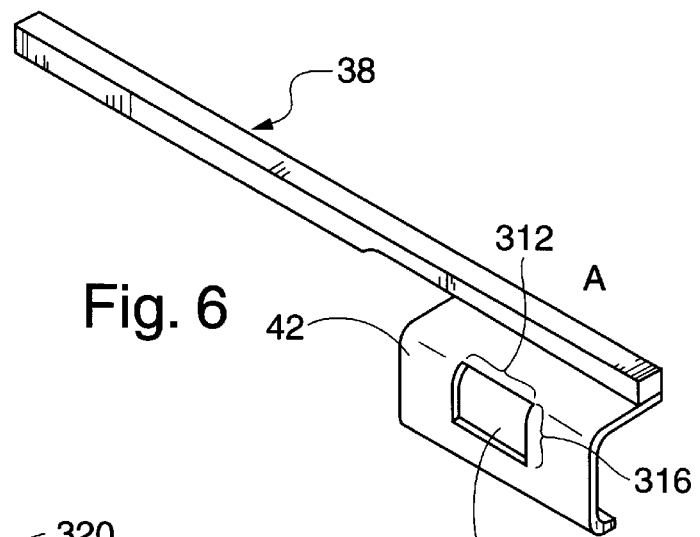
FIGS. 6 and 7 are embodiments of retractor levers useful in cardiac valve replacement surgery.
Figure 7:
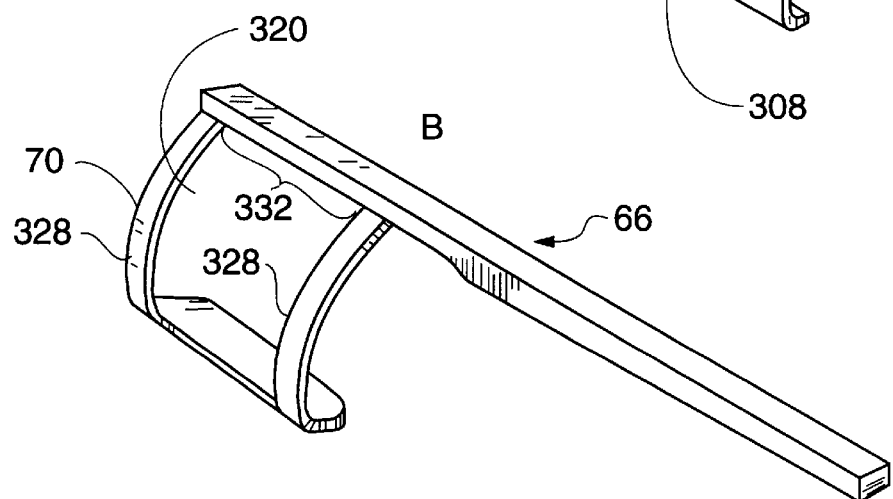
Figure 8:
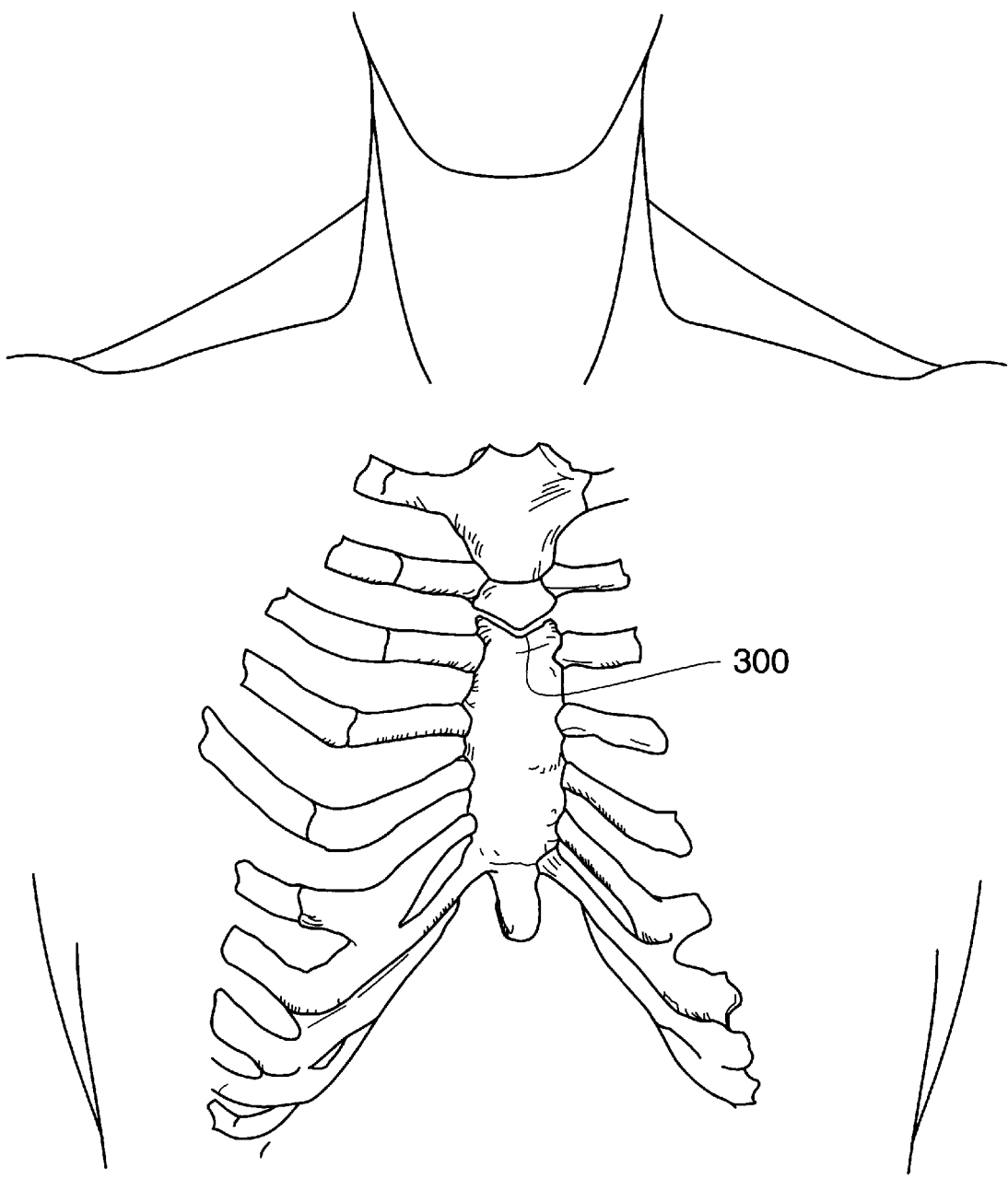
FIG. 8 illustrates the surgical incision made during a cardiac valve replacement surgery.
Figure 9:
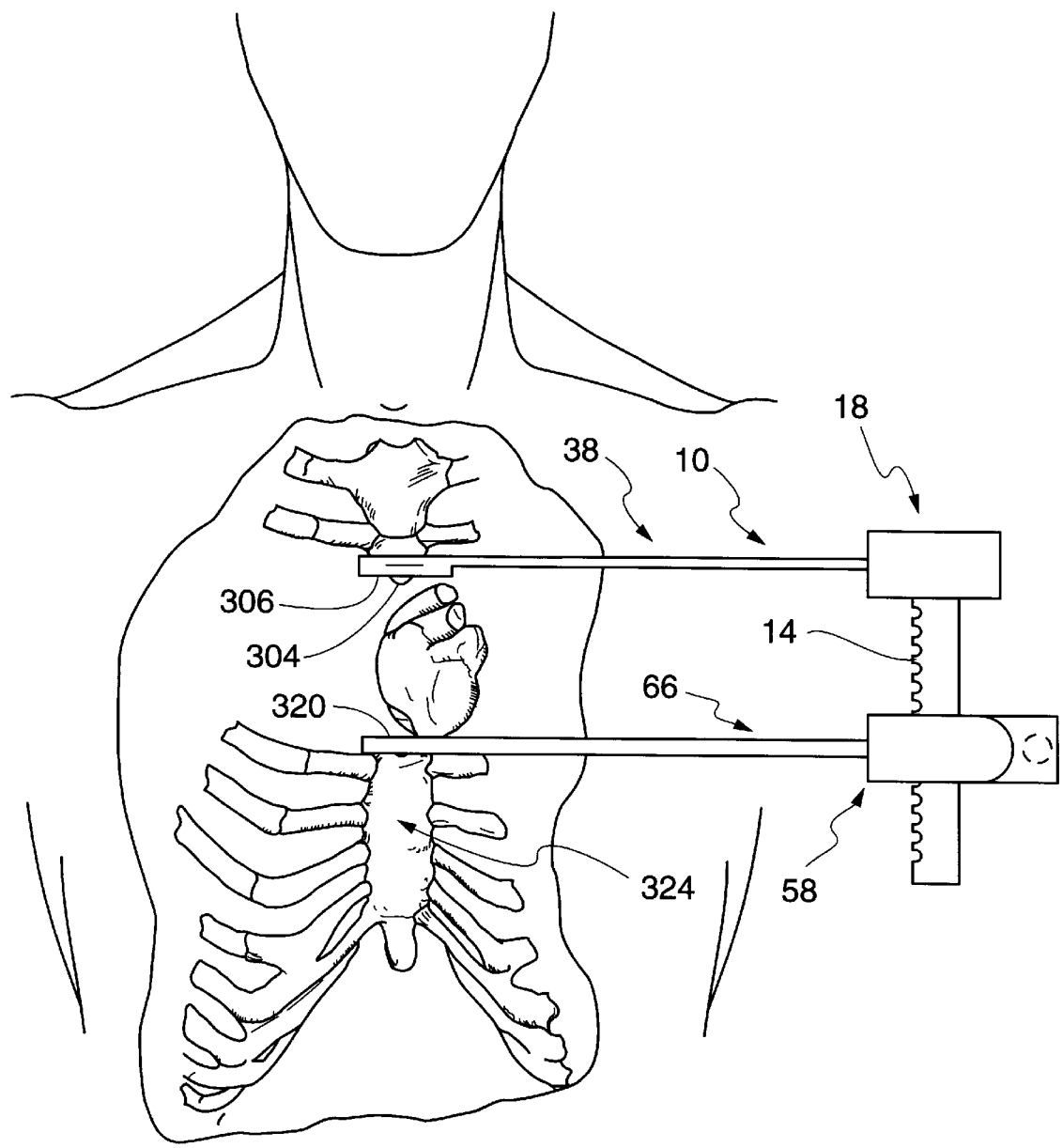
FIG. 9 illustrates the use of the embodiment of the present invention provided in FIGS. 5, 6, and 7 when performing a cardiac valve replacement surgery.

Examples of alternative embodiments of retractor levers 38 and 66 are shown in FIGS. 6 and 7, respectively. The retractor levers of these figures are particularly useful when used together in, for example, cardiac valve replacement surgery, wherein these retractor levers are utilized in separating portions of a patient's sternum that has been surgically severed to gain access to the heart. To illustrate this, reference is additionally made to FIGS. 8 and 9. FIG. 8 shows the configuration of the cut 300 through a patient's sternum during a cardiac valve replacement surgery. FIG. 9 shows how the retractor 10 (e.g., the embodiment of FIG. 5) wherein the retractor levers of FIGS. 6 and 7 are used during this surgery. In particular, the opening 304 of retractor lever 38 (FIG. 6) receives the point 306 of this upper "V", thereby assuring a secure and stable grip for retraction during the surgery. That is, since the opening 304 has a length 312 of about 2 cm and a width 316 of about 1.5 cm, the opening 304 surrounds a sufficiently large mass of the sternum so that for a typical adult it is very unlikely that the grip will accidently disengage from the upper "V".

Referring now to FIGS. 7 and 9, the retractor lever 66 is positioned so that the opening 320 of grip 70 surrounds the entire sternum portion 324 (FIG. 9). That is, the grip retainers 328 retract against the tissue and ribs surrounding the sternum. Thus, during cardiac valve surgery, the sternum is severed, for example, between the second and third ribs and once the retractor levers 38 and 66 are fit to opposite sides of the sternum cut, the grips 42 and 70 are retracted so that grip 42 pushes toward the patient and grip 66 lifts away from the patient (i.e., the embodiment of FIG. 5 is used in FIG. 9 with the crank 86 pointing downward).

Note that as with grip 42, grip 70 is designed to securely and stably grip the ribs and tissue around the lower portion of the sternum.

In an alternative method of use, after selecting the retractor levers and adjusting the spacing between the heads, the surgeon may insert the selected retractor levers into the surgical retractor bores at the desired orientations and then fit the grips onto opposite sides of the incision.

Of course, in either of the above methods, it is an important aspect of the present invention that the surgeon can easily reorient the retractor levers within the retractor heads. That is, since the mating portion of each retractor lever can be easily removed from a receiving bore (22 or 24), the surgeon can reposition a retractor lever within the receiving bore (and thereby change the position of the corresponding tissue grip), or the surgeon can remove the retractor lever from the receiving bore and place the lever's mating portion in an alternative bore within the same head (assuming this head includes at least two bores).

The foregoing discussion of the invention has been presented for purposes of illustration and description. Furthermore, the description is not intended to limit the invention to the form disclosed herein. Consequently, variation and modification commensurate with the above teachings, and the skill and knowledge in the relevant art, are within the scope of the present invention. The embodiment described herein above is further intended to explain the best mode presently known of practicing the invention and to enable others skilled in the art to utilize the invention as such, or in various embodiments, and with various modifications required by their particular applications or uses of the invention. It is intended that the appended claims be construed to include alternate embodiments to the extent permitted by the prior art.

What is claimed is:

1. A surgical retractor for retracting an incision of a patient, comprising:
   a first retractor head having a first bore;
   a second retractor head having at least a second bore;
   a crossbar connecting said first and second retractor heads along a length of said crossbar, wherein at least one of said first and second retractor heads is moveable along the crossbar and said first and second bores are generally transverse to the length of the crossbar and are at different offsets from the crossbar, each of said offsets is substantially coincident with a direction that is outwardly directed away from the patient;
   a first retractor lever having a first grip at one end of a length of the first lever and a first mating portion at an opposite length of the first lever, wherein said first mating portion is receivable within said first bore;
   a second retractor lever having a second grip at one end of a length of the second lever and a second mating portion at an opposite end of the length of the second lever, wherein said second mating portion is receivable within in said second bore;
   wherein when said first and second grips grip, respectively, opposite first and second areas of an incision within the patient, and, when said first and second retractor heads are moved apart, at least one of the following occurs: said first grip lifts the first area outwardly from the patient and the second grip depresses the second area toward the patient.

2. A surgical retractor, as claimed in claim 1, wherein the first retractor head is fixedly attached to the crossbar and said second retractor head is moveable along the length of the crossbar.

3. A surgical retractor, as claimed in claim 1, wherein said first and second bores are substantially parallel.

4. A surgical retractor, as claimed in claim 1, wherein at least one of said first retractor head and said second retractor head include a plurality of bores spaced at different offsets from the crossbar.

5. A surgical retractor, as claimed in claim 4, wherein both of said first retractor head and second retractor head include a plurality of bores wherein the bores within at least one of the first and second retractor heads are parallel.

6. A surgical retractor, as claimed in claim 1, wherein said second retractor head is moveable by a crank that engages teeth on the crossbar.

7. A surgical retractor, as claimed in claim 6, wherein the crank is attached to the second retractor head.

8. A surgical retractor, as claimed in claim 6, wherein said crank includes a crank handle that provides three dimensional rotational movement.

9. A surgical retractor, as claimed in claim 1, wherein at least one of said first and second bores has an interior surface with a plurality of notches for receiving a mating edge on a corresponding one of the first and second retractor levers, wherein a mating of the edge with one of the notches fixes a rotational orientation of the a grip on the corresponding one retractor lever.

10. A surgical retractor, as claimed in claim 1, wherein at least the mating portion of one of the first and second retractor levers is receivable within one of the first and second bores, respectively, for positioning a corresponding one of the first and second grips at a different vector offset from the crossbar than the other of the first and second grips.

11. A surgical retractor, as claimed in claim 1, wherein at least one of said first retractor head and said second retractor head is replaceable by a third retractor head operatively connected to the crossbar.

12. A surgical retractor, as claimed in claim 11, wherein said third retractor head has a different size from one of said first retractor head and said second retractor head.

13. A surgical retractor, as claimed in claim 1, wherein the first bore and the second bore each have one or more notches for mating with the first mating portion and the second mating portion, respectively.

14. A surgical retractor, as claimed in claim 13, wherein the one or more notches in the first bore are rotatable within the first bore and lockable at a plurality of positions within the first bore.

15. A surgical retractor, as claimed in claim 1, wherein the first retractor head is rotatable about an axis parallel to a contour of the length of the crossbar.

16. A surgical retractor, as claimed in claim 1, wherein during cardiac surgery, said first and second grips each have openings through which respective first and second severed portions of a patient's sternum fits.

17. A surgical retractor, as claimed in claim 1, wherein said first portion is further away from the patient's head than the second portion so that during retraction, the first grip lifts the first portion outwardly from the patient and the second grip pushes the second portion toward the patient.

18. A surgical retractor, comprising:
   a first retractor head having a first set of two or more bores;
   second retractor head having a second set of one or more bores;
   a crossbar connecting the first and second retractor heads between a length of the crossbar, wherein at least one bore of said first set and at least a second bore of said second set are:(a) at different vector offsets from the crossbar and (b) at least one of said offsets is substantially coincident with a direction that is outwardly directed away from the patient;
   a first retractor lever having a first grip at one end of a length of the first lever and a first mating portion at an opposite end of the length of the first lever, wherein the first mating portion is receivable within each of the bores of the first set and wherein the first mating portion is adjustably positionable within at least one of the bores of the first set between a plurality of orientations, each of the orientations providing a different position for the first grip;
   second retractor lever having a second grip at the end of a length of the second lever and a second mating portion at an opposite end of the length of the second lever, wherein said second mating portion is operably connected to the second retractor head so that the second retractor lever and the first retractor lever each grips an opposite side of an incision for retraction;
   wherein the two bores of the first set of bores are offset in one of: a different direction from the crossbar and a different distance from the crossbar.

19. A surgical retractor, as claimed in claim 18, wherein the length of the crossbar includes a curved portion.

20. A surgical retractor, as claimed in claim 18, wherein at least one of said first and second retractor heads is angularly adjustable in relation to the length of the crossbar.

21. A method for separating tissue during a surgical operation of a patient, comprising:

operably connecting a first retractor lever to a first retractor head of a surgical retractor so that when separating tissue using a first tissue grip provided by said first retractor lever, said first retractor lever causes a first portion of a crossbar adjacent said first retractor head to be at a first distance outwardly directed from the patient;

selecting a particular bore from a plurality of bores in a second retractor head of the surgical retractor for receiving a second retractor lever, each of said bores being at a different corresponding vector offset from said crossbar wherein, when said second retractor lever is operably connected to said particular bore, a spatial relationship between said particular bore and said crossbar causes a second portion of said crossbar to be at a second distance from the patient, said first and second distances being different;

inserting a first retractor lever into the first bore, wherein the first retractor lever includes a first tissue grip;

operably connecting said second retractor lever in said second particular bore, wherein a a second tissue grip, included in the second retractor lever, is positioned in a desired orientation in relation to the first tissue grip;

inserting said first and second grips into the incision within a patient, wherein said first and second grips grip first and second areas of the incision, respectively;

retracting at least one of the first and second grips by moving, respectively, at least one of the first and second retractor heads along the crossbar, wherein said first and second distances are effective for at least one of the following: said first grip lifting the first area outwardly from the patient and the second grip depressing the second area toward the patient.

22. A surgical retractor for retracting an incision of a patient, comprising:

a first retractor head having a first bore;

a second retractor head having at least a second bore;

a crossbar connecting said first and second retractor heads along a length of said crossbar, wherein at least one of said first and second retractor heads is moveable along the crossbar, and said first and second bores are generally transverse to the length of the crossbar and are at different offsets from the crossbar;

a first retractor lever having a first grip at one end of a length of the first lever and first mating portion at an opposite length of the first lever, wherein said first mating portion is adjustably slidable within said first bore for changing an extent of the length of the first lever extending outside of said first bore;

a second retractor lever having a second grip at one end of a length of the second lever and a second mating portion at an opposite end of the length of the second lever;

wherein when said first and second levers are, respectively, provided in said first and second bores, and said first and second grips grip, respectively, opposite first and second areas of an incision within a patient, and, when said first and second retractor heads are moved apart said different offsets induce at least one of: said first grip lifts the first area outwardly from the patient and the second grip depresses the second area toward the patient.

23. A surgical retractor for retracting an incision of a patient, comprising:

a first retractor head having a first bore;

a second retractor head having at least a second bore;

a crossbar connecting said first and second retractor heads along a length of said crossbar, wherein at least one of said first and second retractor heads is moveable along the crossbar and said first and second bores are generally transverse to the length of the crossbar and are at different offsets from the crossbar, at least one of said offsets being between said crossbar and the patient;

a first retractor lever having a first grip at one end of a length of the first lever and a first mating portion at an opposite length of the first lever, wherein said first mating portion is receivable within said first bore;

a second retractor lever having a second grip at one end of a length of the second lever and a second mating portion at an opposite end of the length of the second lever, wherein said second mating portion is receivable within in said second bore;

wherein when said first and second grips grip, respectively, opposite first and second areas of an incision within the patient, and, when said first and second retractor heads are moved apart, at least one of the following occurs: said first grip lifts the first area outwardly from the patient and the second grip depresses the second area toward the patient.

24. A surgical retractor, comprising:

a first retractor head having a first bore;

a second retractor head having at least a second bore;

a crossbar connecting said first and second retractor heads along a length of said crossbar, wherein at least one of said first and second retractor heads is moveable along the length of the crossbar and said first and second bores are generally transverse to the length of the crossbar and there is a first offset from the patient between said first bore and a first portion of said crossbar adjacent to said first retractor head, and a second offset from the patient between said second bore and a second portion of said crossbar adjacent to said second retractor head, said second offset being different from said first offset;

a first retractor lever having a first grip at one end of a length of the first lever and a first mating portion at an opposite length of the first lever, wherein said first mating portion is receivable within said first bore;

a second retractor lever having a second grip at one end of a length of the second lever and a second mating portion at an opposite end of the length of the second lever, wherein said second mating portion is receivable within in said second bore;

wherein when said first and second grips grip, respectively, opposite first and second areas of an incision within the patient, and, when said first and second retractor heads are moved apart, said first and second offsets induce said first portion and said second portion to be at sufficiently different distances from the patient so that at least one of the following occurs: said first grip lifts the first area outwardly from the patient, and the second grip depresses the second area toward the patient.

25. A surgical retractor, comprising:

a first retractor head having a first bore;

a second retractor head having at least a second bore;

a crossbar having a length and a width defining a plane that is spaced apart from a patient's body upon which the surgical retractor is utilized, wherein said crossbar connects said first and second retractor heads along the length of said crossbar, wherein at least one of said first and second retractor heads is moveable along the crossbar, and at least one of said first and second bores is transverse to at least a portion of the width of the crossbar and said first and second bores are at different offsets from the crossbar;

a first retractor lever having a first grip at one end of a length of the first retractor lever and a first mating portion at an opposite length of the first retractor lever, wherein said first mating portion is receivable within said first bore;

a second retractor lever having a second grip at one end of a length of the second retractor lever and a second mating portion at an opposite end of the length of the second retractor lever, wherein said second mating portion is receivable within said second bore;

wherein when said first and second grips contact, respectively, opposite first and second areas of an incision within a patient, and said first and second retractor heads are moved apart, at least one of the following occurs: said first grip lifts the first area outwardly from the patient and the second grip depresses the second area toward the patient.

26. A surgical retractor for retracting an incision of a patient, comprising:

a first retractor head having a first attachment portion for attaching a retractor lever to said first retractor head;

a second retractor head having a second attachment portion for attaching a retractor lever to said second retractor head;

a crossbar operably connected to said first and second retractor heads so that said first and second retractor heads are capable of being adjustably spaced apart along a length of said crossbar, and said first attachment portion is a first distance from said crossbar and said second attachment portion is a different second distance from said crossbar;

a first retractor lever having a first length with a first tissue grip at one end of the first length and a first mating end at an opposite end of the first length, said first mating end for mating with said first attachment;

a second retractor lever having a second length with a second tissue grip at one end of the second length and a second mating end at an opposite end of the second length, said second mating end for mating with said second attachment;

wherein a mating of said first attachment and said first mating end provides a first portion of said crossbar adjacent said first retractor head to be at least said first distance from the patient when said first tissue grip grips a first side of the incision, and a mating of said second attachment and said second mating end provides a second portion of said crossbar adjacent said second retractor head to be at least said second distance from the patient when said second tissue grip grips a second side of the incision, and said first and second distances are sufficiently different to cause one of: said first tissue grip to lift the first side of the incision in a direction outwardly from the patient, and said second grip to depress the second side of the incision in a direction toward the patient.

* * * * *